United States Patent [19]

Greve et al.

[11] 4,075,409
[45] * Feb. 21, 1978

[54] BENZOPHENONE DERIVATIVES

[75] Inventors: Heinz Günter Greve; Klaus Resag, both of Frankfurt am Main, Germany

[73] Assignee: Cassella Farbwerke Mainkur Aktiengesellschaft, Germany

[*] Notice: The portion of the term of this patent subsequent to May 20, 1992, has been disclaimed.

[21] Appl. No.: 516,428

[22] Filed: Oct. 21, 1974

[30] Foreign Application Priority Data

Nov. 10, 1973 Germany .............................. 2356239

[51] Int. Cl.$^2$ ............................................ C07C 103/50
[52] U.S. Cl. ............................... 560/36; 260/552 R; 260/553 A; 260/558 A; 260/562 N; 424/300; 424/309; 424/322; 424/324; 560/9; 560/21; 560/27
[58] Field of Search .................................... 260/471 A

[56] References Cited

U.S. PATENT DOCUMENTS 3,888,899  6/1975  Greve et al. ............... 260/471 A X
3,928,415  12/1975 Greve et al. ............... 260/471 A X Primary Examiner—Richard L. Raymond
Attorney, Agent, or Firm—Berman, Aisenberg & Platt

[57] ABSTRACT

The present invention relates to pharmacologically valuable new benzophenone derivatives having a pronounced sedative action on the central nervous system and some of which also possess muscle-relaxing and aggression-inhibiting properties. These new derivatives have the structural formula

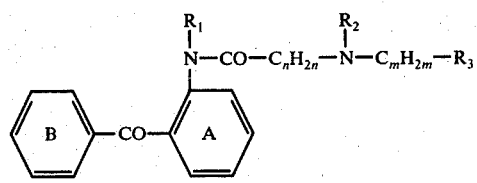

and the pharmaceutically-acceptable acid-addition salts thereof in which
  $R_1$ and $R_2$ are substituents selected from the group consisting of hydrogen, saturated and unsaturated alkyl groups having 1–4 carbon atoms; $R_3$ is selected from the group consisting of —COOC$_3$H$_7$, —COOC$_4$H$_9$, —COOC$_6$H$_5$, —C$_6$H$_5$,

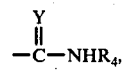

whereby $R_4$ is an aliphatic radical with 1 to 4 carbon atoms or phenyl and Y is an oxygen or sulfur atom; if m is 0 $R_3$ is further selected from the group consisting of —COOCH$_3$ and —COOC$_2$H$_5$; $n$ is an integer selected from 1 and 2; and $m$ is an integer selected from 0, 1, 2 and 3, and wherein the rings A and B may be substituted, ring A being substituted preferably with halogen, such as chlorine, or with nitro, trifluoromethyl, methyl, methoxy or methylmercapto, preferably in the 5-position, and ring B being preferably substituted in the 2'-position with chlorine or fluorine. The radicals $R_1$ and $R_2$ preferably signify hydrogen or a methyl group, or a n-butyl group in the case of Ring B.

Compounds represented by the above structural formula may be produced by reacting a compound represented by the formula

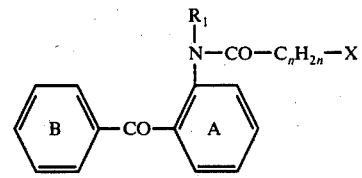

with a compound having the formula Y — C$_m$H$_{2m}$ — R$_3$, one of X and Y signifying the substituent R$_2$ — NH — and the other signifying a halogen atom, preferably a bromine or chlorine atom, so as to form the above specified benzophenone derivative with the elimination of H — Hal; $R_1$, $R_2$, $R_3$, $n$ and $m$ being as defined above, and the rings A and B being optionally substituted as discussed above. The hydrogen halide which is eliminated is advantageously bound by the addition of an acid-binding agent, as for example, a molar excess of the amine used in the reaction or, for example, triethylamine, dimethylaniline, potassium or sodium carbonate or sodium bicarbonate. The reaction is carried out in a suitable solvent, preferably at an elevated temperature, typically the reflux temperature of the solvent used.

5 Claims, No Drawings

BENZOPHENONE DERIVATIVES

The invention relates to pharmacologically valuable new benzophenone derivatives of the general formula I

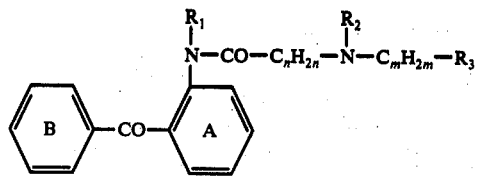

and the pharmaceutically-acceptable acid-addition salts thereof, in which $R_1$ and $R_2$ are selected from the group consisting of hydrogen or a saturated or unsaturated alkyl radical with 1 to 4 carbon atoms, $R_3$ is selected from the group consisting of —$COOC_3H_7$, —$COOC_4H_9$, —$COOC_6H_5$, —$C_6H_5$ and

wherein $R_4$ is an aliphatic radical with 1 to 4 carbon atoms or phenyl, and Y is an oxygen or sulfur atom; when $m$ is 0, $R_3$ is further selected from the group consisting of —$COOCH_3$ and —$COOC_2H_5$, $n$ is 1 or 2, $m$ is 0, 1, 2 or 3, and the rings A and B may be substituted.

Preferred substituents for the ring A are halogen, especially chlorine, nitro, trifluoromethyl, methyl, methoxy or methylmercapto, and substitution is preferably in the 5-position; and preferred substituents for the ring B are fluorine or chlorine, substitution preferably being at the 2'-position. The radicals $R_1$ and $R_2$ preferably signify hydrogen or a methyl group, or an n-butyl group in the case of $R_2$.

The invention also extends to processes for the production of compounds of the general formula I.

Compounds of the general formula I may be produced by reacting a benzophenone derivative of the general formula

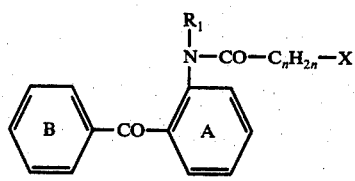

with a compound of the general formula III

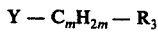 III one of X and Y signifying the radical $R_2$—NH— and the other signifying a halogen atom, preferably a bromine or chlorine atom, so as to form a compound of the general formula I with the elimination of H—Hal, $R_1$, $R_2$, $R_3$, $n$ and $m$ being as defined above, and the rings A and B being optionally substituted as discussed above. The reaction is preferably carried out in an inert solvent, e.g. an ether, a ketone, an aromatic or aliphatic hydrocarbon or halogenated hydrocarbon. Suitable ethers include, for example, dioxan and tetrahydrofuran; suitable ketones include, for example, acetone, methyl ethyl ketone and methyl isobutyl ketone; suitable aromatic hydrocarbons include, for example, benzene, toluene and xylene; a suitable aliphatic hydrocarbon mixture is, for example, petroleum ether; and suitable halogenated hydrocarbons include, for example, chloroform and carbon tetrachloride. The reaction can be carried out at temperatures of 5° C up to the boiling point of the solvent, the reaction time being shorter at the higher reaction temperatures, which are in fact normally used. Mixtures of various individual solvents can also be used as the solvent for the present reaction. The reaction is preferably carried out at the reflux temperature of the solvent.

The hydrogen halide which has been eliminated between compounds II and III is preferably disposed of by the addition of an acid-binding agent. A molar excess of an amine, for example the amine employed for the reaction, or, for example, triethylamine or dimethylaniline, or, again, an alkali metal carbonate or bicarbonate (e.g. potassium carbonate or sodium carbonate or sodium bicarbonate) can serve as such an acid-binding agent. The amine reactant can also be employed in the form of an acid-addition salt. A further mol of triethylamine, dimethylaniline or the like is then required to liberate the amine which is to be reacted. It may be appropriate to carry out the reaction under an inert atmosphere, for example under nitrogen.

Starting compounds of the general formula II, in which X signifies a halogen atom, can easily be produced from aminobenzophenones of the general formula IV

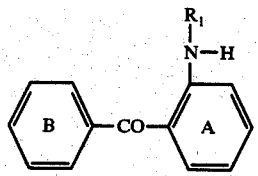

by reaction with a halogenacyl halide of the general formula V

wherein Hal is a halogen atom, preferably a bromine or chlorine atom.

The initial compounds of the general formula II, in which X signifies the radical $R_2$—NH—, can be obtained by reacting a compound of the general formula IIa

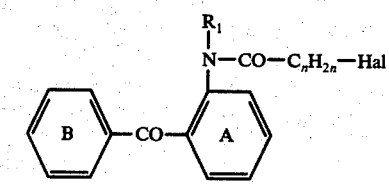

wherein Hal is a halogen atom, preferably a bromine or chlorine atom, with an amine of the general formula VI

 VI

The reaction is preferably carried out at a temperature between 5° and 50° with a reaction time of from a few hours up to several days, advantageously in a suitable solvent.

Those compounds of the general formula I, in which $m$ signifies 2 or 3 and $R_1$, $R_2$, $R_3$ and $n$ are as defined above, may be produced by an addition reaction between a benzophenone derivative of the general formula II, in which X signifies $R_2$—NH—, and a compound containing an aliphatic double bond and of the general formula VII

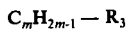  VII in which $m$ means the number 2 or 3. The reaction is preferably carried out in a suitable solvent at room temperature or elevated temperature. Examples of suitable solvents are alcohols, ethers, ketones, hydrocarbons and acid amides. Suitable ethers include, for instance, dioxan and tetrahydrofuran; suitable ketones include, for instance, acetone, methyl ethyl ketone and methyl isobutyl ketone; suitable aromatic hydrocarbons include, for instance, benzene, toluene and xylene; a suitable aliphatic hydrocarbon mixture is, for example, petroleum ether; suitable halogenated hydrocarbons include, for instance, chloroform and carbon tetrachloride; and suitable acid amides include dimethylformamide and dimethylacetamide. The reaction can be carried out at temperatures of 5° C up to the boiling point of the solvent, the reaction time being shorter at the higher reaction temperatures, which are in fact normally used. The reaction is preferably carried out at the reflux temperature of the solvents. Mixtures of various individual solvents can also be used as the solvent for the present reaction.

Compounds according to the invention wherein, in the general formula I, $m = 0$ and $R_3$ is —(CY)NHR$_4$ can be prepared only with very great difficulty by the first method of preparation described above, and cannot be prepared at all by the second method of preparation described above. These compounds can, however, be prepared in a simple manner by reacting a benzophenone derivative of the general formula VIII

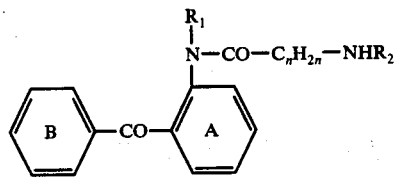  VIII with a compound of the general formula IX

  IX

The reaction is preferably carried out in an inert solvent, e.g. an ether, a ketone, an aromatic or aliphatic hydrocarbon, or a halogenated hydrocarbon. Suitable ethers include, for instance, dioxan and tetrahydrofuran; suitable ketones include, for instance, acetone, methyl ethyl ketone and methyl isobutyl ketone; suitable aromatic hydrocarbons include, for instance, benzene, toluene and xylene; a suitable aliphatic hydrocarbon mixture is, for example, petroleum ether; and suitable halogenated hydrocarbons include, for instance, chloroform and carbon tetrachloride. It is also possible to use a solvent which can react with one of the reactants under different reaction conditions but which does not react therewith under the reaction conditions actually employed. Thus, alcohols (e.g. ethanol) can react with isocyanates or isothiocyanates of the general formula IX, but in the presence of a compound of the general formula VIII no reaction takes place between an isocyanate or isothiocyanate of the general formula IX and an alcohol used as a solvent. The reaction can be carried out at temperatures of 5° C up to the boiling point of the solvent, the reaction time being shorter at the higher reaction temperatures, which are in fact normally used. Mixtures of various individual solvents can also be used as the solvent for the present reaction. The reaction is preferably carried out at the reflux temperature of the solvent.

The compounds of the general formula VIII, which are equivalent to those compounds of the general formula II wherein X is $NHR_2$, may be prepared by reacting a compound IIa with a compound VI as described earlier. The compounds of the general formula IX are isocyanates when $Y = O$ and isothiocyanates when $Y = S$, and these isocyanates and isothiocyanates are known compounds.

Compounds according to the invention wherein, in the general formula I, $R_3$ is —(CO)NHR$_4$ can also be obtained by reacting a compound of the general formula X

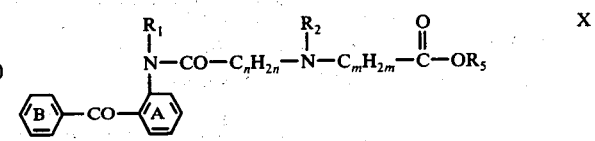  X wherein $R_5$ is an alkyl radical, in particular one with 1 to 4 C atoms, or an aryl radical, in particular a phenyl radical, with an amine of the general formula XI

  XI

In this reaction an alcohol HOR$_5$ is eliminated between the compounds X and XI. When $m = 0$ and $R_5 = -C_6H_5$, the reaction takes place particularly readily even at room temperature. In other cases it is preferably carried out at elevated temperature.

Suitable inert solvents which can be used are, for example, ethers, ketones, aromatic or aliphatic hydrocarbons or halogenated hydrocarbons. Suitable ethers include, for instance, dioxan and tetrahydrofuran; suitable ketones include, for instance, acetone, methyl ethyl ketone and methyl isobutyl ketone; suitable aromatic hydrocarbons include, for instance, benzene, toluene and xylene; a suitable aliphatic hydrocarbon mixture is, for example, petroleum ether; and suitable halogenated hydrocarbons include, for example, chloroform and carbon tetrachloride. Mixtures of various individual solvents can also be used as the solvent of the present reaction. The reaction is preferably carried out at the reflux temperature of the solvent.

The compounds according to the invention are mostly oily substances, but can be converted in the usual manner to crystalline acid-addition salts.

Pharmaceutically-acceptable acid-addition salts include hydrochlorides, hydrobromides, sulphates, phosphates, lactates, maleates, malates, fumarates, oxalates, glycolates, citrates, tartrates and acetates.

The compounds of the present invention having the general formula I and their pharmaceutically-acceptable salts are distinguished by valuable pharmacological properties, in particular a marked depressant action on the central nervous system. Some of these compounds also possess muscle-relaxing and aggression-inhibiting properties. The compounds, of the general formula I, of the present invention and their pharmaceutically-acceptable salts are therefore valuable medicaments; they can be used as medicaments either directly or in the form of their pharmaceutically-acceptable salts. The pharmaceutical preparations can be prepared, for example as tablets, suppositories, capsules, emulsions or suspensions, in a manner which is in itself known by using pharmaceutical excipients, which do not react with the compounds. Any substance suitable for the intended purpose can be used as a pharmaceutical excipient, for example talc, starch, vegetable oils, petroleum jelly and the like. The pharmaceutical preparations can optionally also contain other therapeutically-active substances.

The pharmacological examination of the central depressant (sedative) action was carried out on albino mice with the aid of the climbing test described by P. K. KNEIP: Arch. int. pharmacodyn 126, 238 (1960) and R. DOMENJOZ and W. THEOBALD: Arch. int. pharmacodyn 120, 450 (1959).

The results of the pharmacological examinations which were carried out are summarised in the table which follows. In the final column of the table, the percentage of the experimental animals which no longer embark on the climbing work, which is normally readily undertaken, is given under the heading "Central depressant action in %".

| Preparation | $LD_{50}$ g/kg mice intraperitoneally | Dose mg/kg orally | Central depressant action in % |
|---|---|---|---|
| 2-(3-Ethoxycarbonyl)-N-methyl-3-aza-propanamido)-5-nitro-benzophenone | 0.500 | 10.0 | 70 |
| 2-(3-Ethoxycarbonyl-N-methyl-3-aza-propanamido)-5-chlorobenzophenone | 0.270 | 4.0 | 30 |
| DL-2-(5-Phenyl-N-methyl-4-methyl-3-aza-pentanamido)-5-chlorobenzophenone | 0.240 | 8.0 | 40 |
| DL-2-(5-Phenyl-N-methyl-4-methyl-3-aza-pentanamido)-5-nitro-benzophenone | 0.044 | 8.0 | 50 |
| 2-(3-Ethoxycarbonyl-N-methyl-3-aza-propanamido)-2',5-dichlorobenzophenone | 0.240 | 8.0 | 90 |
| 2-(5-n-Butylaminocarbonyl-N-methyl-3-n-butyl-3-aza-pentanamido)-5-nitro-benzophenone | 0.500 | 8.0 | 50 |
| DL-2-(5-Phenyl-N-methyl-4-methyl-3-aza-pentanamido)-2'-5-dichloro-benzophenone | 0.024 | 8.0 | 70 |
| 2-(3-Phenylamino-thiocarbonyl-3-aza-3-methyl-propanamido)-5-chlorobenzophenone | >1,000 | 8.0 | 50 |
| Comparison preparation: Meprobamate | 0.620 | 70 | 50 |

The benzophenone derivatives were tested in the form of their hydrochlorides.

In the following examples, the temperatures are given in degrees Centigrade. The abbreviation "D" in the melting point data denotes decomposition.

EXAMPLE 1

7.3 g of 2-(N-methyl-bromoacetamido)-5-chlorobenzophenone are heated in 200 ml of anhydrous xylene with 2.2 g of triethylamine and 2 g of urethane ($NH_2COOC_2H_5$) for 12 hours under reflux whilst stirring. The triethylamine hydrobromide which has precipitated is filtered off with suction after cooling, the filtrate is extracted by shaking with three times 250 ml of water and the organic phase is dried over potassium carbonate, filtered and evaporated in vacuo. The oily residue is dissolved in 400 ml of anhydrous diethyl ether and filtered and 6.5 g of 2-(3-ethoxycarbonyl-N-methyl-3-aza-propanamido)-5-chlorobenzophenone hydrochloride (79% of theory), with a melting point of 156°–158°, are obtained by passing dry hydrogen chloride gas into the ethereal solution.

The compounds described in the tables which follow are prepared in an analogous manner, as indicated in Example 1:

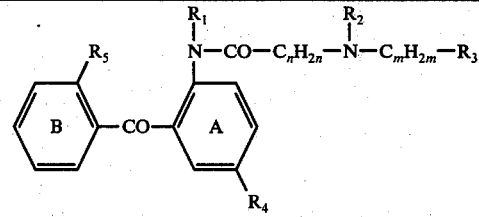

| $R_1$ | $C_nH_{2n}$ | $R_2$ | $R_3$ | $C_mH_{2m}$ | $R_4$ | $R_5$ | Melting point of the hydrochloride |
|---|---|---|---|---|---|---|---|
| $CH_3$ | $-CH_2-$ | H | $-CO-OC_2H_5$ | — | $NO_2$ | H | 139–141° |
| $CH_3$ | $-CH_2-$ | H | $-CO-OC_2H_5$ | — | $CH_3$ | H | 100–102° (D) |
| $CH_3$ | $-CH_2-$ | H | $-CO-OC_2H_5$ | — | $OCH_3$ | H | 115–117° |
| $CH_3$ | $-CH_2-$ | H | $-CO-OC_3H_7$ | $-CH_2-CH_2-CH_2-$ | Cl | H | 114–116° (D) |
| $CH_3$ | $-CH_2-$ | H | $-CO-OC_3H_7$ | $-CH_2-CH_2-CH_2-$ | $NO_2$ | H | 88–90° |
| $CH_3$ | $-CH_2-$ | H | $-CO-OC_3H_7$ | $-CH_2-CH_2-$ | Cl | H | 137–139° (D) |
| $CH_3$ | $-CH_2-$ | H | $-CO-OC_3H_7$ | $-CH_2-CH_2-$ | $NO_2$ | H | 121–123° |
| $CH_3$ | $-CH_2-$ | H | $-CO-OC_4H_9$ | $-CH_2-CH_2-$ | Cl | H | 107–109° |
| $CH_3$ | $-CH_2-$ | H | $-CO-OC_4H_9$ | $-CH_2-CH_2-$ | $NO_2$ | H | 116–118° |
| $CH_3$ | $-CH_2-CH_2-$ | H | $-CO-OC_3H_7$ | $-CH_2-CH_2-CH_2-$ | Cl | H | 145–147° |
| $CH_3$ | $-CH_2-$ | H | $-CO-OC_4H_9$ | $-CH_2-$ | Cl | H | 115–118° |
| $CH_3$ | $-CH_2-$ | H | $-CO-OC_4H_9$ | $-CH_2-$ | $NO_2$ | H | 126–129° |
| $CH_3$ | $-CH_2-$ | H | $-CO-OC_2H_5$ | — | Cl | Cl | 74–76° |

-continued

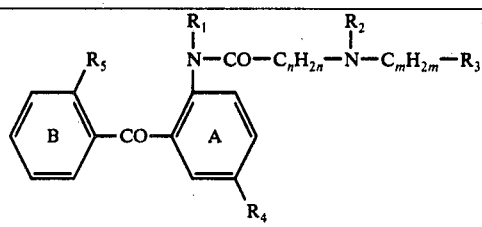

| $R_1$ | $C_nH_{2n}$ | $R_2$ | $R_3$ | $C_mH_{2m}$ | $R_4$ | $R_5$ | |
|---|---|---|---|---|---|---|---|
| $CH_3$ | $-CH_2-$ | H | $-CO-OC_2H_5$ | — | H | H | 80–81° (D) |

| $R_1$ | $C_nH_{2n}$ | $R_2$ | $R_3$ | $C_mH_{2m}$ | $R_4$ | $R_5$ | Melting point of the tartrate |
|---|---|---|---|---|---|---|---|
| $CH_3$ | $-CH_2-$ | H | $-CO-OC_4H_9$ | $-CH_2-CH_2-CH_2-$ | Cl | H | 79–82° (D) |

The $CO-OC_3H_7$ and $-CO-OC_4H_9$ radicals representing $R_3$ in the above tables are n-propoxycarbonyl and n-butoxycarbonyl radicals, respectively.

EXAMPLE 2

A mixture of 16.1 g of 2-(methyl-chloroacetamido)-5-chlorobenzophenone, 10 g of triethylamine and 7.6 g of 3-methylaminopropionic acid methylamide hydrochloride in 500 ml of anhydrous xylene is heated to reflux for 12 hours whilst stirring. The triethylamine hydrochloride which has precipitated is filtered off with suction after cooling and, after extracting three times by shaking with water, the organic phase is dried over anhydrous potassium carbonate, filtered and evaporated in vacuo. The oily crude base thus obtained (18 g) is dissolved in 800 ml of anhydrous diethyl ether and filtered and 17.0 g of 2-(5-methylaminocarbonyl-N-methyl-3-methyl-3-aza-pentanamido)-5-chlorobenzophenone hydrochloride (77% of theory), with a melting point of 151°–153°, are obtained by passing dry hydrogen chloride into the solution.

The compounds described in the table which follows are prepared in an analogous manner, as indicated in Example 2:

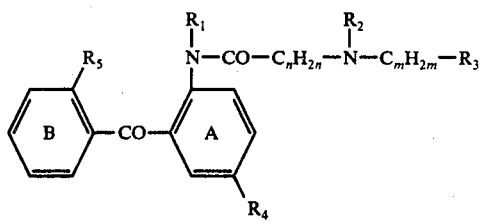

| $R_1$ | $C_nH_{2n}$ | $R_2$ | $R_3$ | $C_mH_{2m}$ | $R_4$ | $R_5$ | Melting point of the hydrochloride |
|---|---|---|---|---|---|---|---|
| $CH_3$ | $-CH_2-$ | $CH_3$ | $-CO-NH-CH_3$ | $-CH_2-CH_2-$ | $NO_2$ | H | 150–152° |
| $CH_3$ | $-CH_2-$ | $CH_2-CH=CH_2$ | $-CO-NH-CH_2-CH=CH_2$ | $-CH_2-CH_2-$ | Cl | H | 103–106° (D) |
| $CH_3$ | $-CH_2-$ | $CH_2-CH=CH_2$ | $-CO-NH-CH_2-CH=CH_2$ | $-CH_2-CH_2-$ | $NO_2$ | H | 120–122° |
| $CH_3$ | $-CH_2-$ | $(n)C_4H_9$ | $-CO-NH-_{(n)}C_4H_9$ | $-CH_2-CH_2-$ | Cl | H | 129–131°(D) |
| $CH_3$ | $-CH_2-$ | $(n)C_4H_9$ | $-CO-NH-_{(n)}C_4H_9$ | $-CH_2-CH_2-$ | $NO_2$ | H | 132–134° |
| $CH_3$ | $-CH_2-CH_2-$ | $CH_2-CH=CH_2$ | $-CO-NH-CH_2-CH=CH_2$ | $-CH_2-CH_2-$ | Cl | H | 130–132° |
| $CH_3$ | $-CH-$<br>$\;\;\;\|$<br>$\;\;CH_3$ | $nC_4H_9$ | $-CO-NH-_{(n)}C_4H_9$ | $-CH_2-CH_2-$ | Cl | H | 111–113° |
| $CH_3$ | $-CH_2-$ | $CH_3$ | $-CO-NH-CH_3$ | $-CH_2-CH-$<br>$\;\;\;\;\;\;\;\;\;\;\|$<br>$\;\;\;\;\;\;\;\;\;\;CH_3$ | Cl | H | 173–175° |
| $CH_3$ | $-CH_2-$ | $CH_3$ | $-CO-NH-CH_3$ | $-CH_2-CH-$<br>$\;\;\;\;\;\;\;\;\;\;\|$<br>$\;\;\;\;\;\;\;\;\;\;CH_3$ | Cl | Cl | 171–173° |
| $CH_3$ | $-CH_2-$ | $CH_3$ | $-CO-NH-CH_3$ | $-CH-CH_2-$<br>$\;\|$<br>$CH_3$ | Cl | H | 147–150° |
| $CH_3$ | $-CH_2-$ | $CH_3$ | $-CO-NH-CH_3$ | $-CH_2-CH-$<br>$\;\;\;\;\;\;\;\;\;\;\|$<br>$\;\;\;\;\;\;\;\;\;\;CH_3$ | $NO_2$ | H | 155–157° |
| $CH_3$ | $-CH_2-$ | $CH_3$ | $-CO-NH-CH_3$ | $-CH-CH_2-$<br>$\;\|$<br>$CH_3$ | $NO_2$ | H | 168–171° |
| $CH_3$ | $-CH_2-$ | $CH_3$ | $-CO-NH-CH_3$ | $-CH-CH_2-$<br>$\;\|$<br>$CH_3$ | Cl | Cl | 157–160° |

EXAMPLE 3

8 g of 2-(methyl-chloroacetamido)-5-chlorobenzophenone and 6.8 g of DL-amphetamine (= DL 1-phenyl-2-aminopropane) in 150 ml of anhydrous dioxan are heated to reflux for 4 hours whilst stirring. The turbid solution is filtered after cooling and evaporated in vacuo and the oily residue is triturated with three times 100 ml of water and dried in vacuo. The oily crude base (8.3 g) thus obtained is dissolved in 400 ml of anhydrous diethyl ether and filtered. 6.5 g of DL-2-(5-phenyl-N-methyl-4-methyl-3-aza-pentanamido)-5-chlorobenzophenone hydrochloride (58% of theory), with a melting point of 132°–135°, are obtained by passing in dry hydrogen chloride gas.

DL-2-(5-Phenyl-N-methyl-4-methyl-3-aza-pentanamido)-5-nitrobenzophenone hydrochloride, with a melting point of 134°–137°, and DL-2-(5-phenyl-N-methyl-4-methyl-3-aza-pentanamido)-2′,5-dichlorobenzophenone hydrochloride, with a melting point of 94°–96°, were obtained in an analogous manner.

EXAMPLE 4

3 g of 2-(methylamino-acetamido)-5-chlorobenzophenone are dissolved in 30 ml of absolute ethanol, 2.6 g of the n-butyl ester of acrylic acid are added and, after the addition of 3 drops of piperidine, the mixture is stirred for 3 hours at room temperature and then for 6 hours under reflux. After cooling, a further 2.6 g of the n-butyl ester of acrylic acid and 3 drops of piperidine are added and the mixture is stirred for a further 10 hours under reflux. After cooling, the solution is filtered and evaporated in vacuo. The oily residue is dissolved in 2 N hydrochloric acid, extracted with ether and then rendered alkaline with potassium carbonate, while cooling well. The mixture is extracted with methylene chloride and the combined organic extracts are washed with water and then dried over anhydrous potassium carbonate. The dry solution is filtered and evaporated in vacuo and the oily residue is dried in vacuo. The crude base (3.3 g) thus obtained is dissolved in 100 ml of anhydrous diethyl ether and filtered. 2.8 g of 2-(5-n-butoxycarbonyl-3-aza-3-methyl-pentanamido)-5-chlorobenzophenone hydrochloride (60% of theory), with a melting point of 92° (D), are obtained by passing dry hydrogen chloride gas into the solution.

EXAMPLE 5

3 g of 2-(methylamino-acetamido)-5-chlorobenzophenone are dissolved in 50 ml of absolute benzene, the solution is filtered and 1.2 g of phenylisocyanate are added. After the addition of 3 drops of piperidine, the mixture is heated to reflux for 1 hour whilst stirring. After cooling, the crystals which have precipitated are filtered off, washed with petroleum ether and dried in vacuo at 50°. In this way 3.1 g of 2-(3-phenylaminocarbonyl-3-aza-3-methylpropanamido)-5-chlorobenzophenone (74% of theory), with a melting point of 145°–147°, are obtained.

2-(3-Methallylaminocarbonyl-3-aza-3-methyl-propanamido)-5-chlorobenzophenone, with a melting point of 100°–101°, 2-(3-ethylaminocarbonyl-3-aza-3-methyl-propanamido)-5-chlorobenzophenone, with a melting point of 170°–171°, and 2-(3-isopropylaminocarbonyl-3-aza-3-methyl-propanamido)-5-chlorobenzophenone, with a melting point of 122°–123°, were prepared in an analogous manner.

2-(3-Phenylaminothiocarbonyl-3-aza-3-methyl-propanamido)-5-chlorobenzophenone, with a melting point of 160°–161°, was obtained with phenylisothiocyanate in an analogous manner in a solvent consisting of 80% of benzene and 20% of chloroform.

EXAMPLE 6

3 g of 2-(methylamino-acetamido)-5-chlorobenzophenone are dissolved in 30 ml of absolute ethanol and filtered. After the addition of 1.2 g of phenylisocyanate, the mixture is heated to reflux for 45 minutes whilst stirring. After cooling, the crystals which have precipitated are filtered off, washed with petroleum ether and dried in vacuo at 50°. In this way 3.4 g of 2-(3-phenylaminocarbonyl-3-aza-3-methyl-propanamido)-5-chlorobenzophenone (80% of theory), with a melting point of 147°–148°, are obtained.

2-(3-Phenylaminothiocarbonyl-3-aza-3-methyl-propanamido)-5-chlorobenzophenone, with a melting point of 159°–160°, was obtained with phenylisothiocyanate in an analogous manner in absolute ethanol as the solvent.

2-(3-Allylaminothiocarbonyl-3-aza-3-methyl-propanamido)-5-chlorobenzophenone, with a melting point of 143°–145°, 2-(3-phenylaminothiocarbonyl-3-aza-propanamido)-2′,5-dichlorobenzophenone, with a melting point of 185°–187°, and 2-(3-allylaminothiocarbonyl-3-aza-propanamido)-2′,5-dichlorobenzophenone, with a melting point of 178°–180°, were prepared in an analogous manner.

What we claim is:

1. A benzophenone derivative having the following structural formula

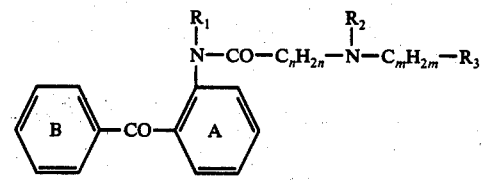

or a pharmaceutically-acceptable acid-addition salt thereof, in which each of $R_1$ and $R_2$ is, independently, a member selected from the group consisting of hydrogen and a saturated or unsaturated alkyl radical with from 1 to 4 carbon atoms, $R_3$ is a member selected from the group consisting of $—COOC_3H_7$, $—COOC_4H_9$ and $—COOC_6H_5$, $n$ is 1 or 2, $m$ is 1, 2 or 3, ring A is optionally substituted with a substituent selected from the group consisting of halogen, nitro, trifluoromethyl, methyl and methoxy, and ring B is optionally substituted with a substituent selected from the group consisting of chloro and fluoro.

2. A benzophenone derivative according to claim 1, wherein ring A is substituted at the 5-position and ring B is substituted at the 2′-position.

3. A benzophenone derivative according to claim 1, wherein $R_1$ is a member selected from the group consisting of hydrogen and methyl, and $R_2$ is a member selected from the group consisting of hydrogen, methyl and butyl.

4. The compound which is 2-(4-n-butoxycarbonyl-N-methyl-3-aza-butanamido)-5-chlorobenzophenone or a pharmaceutically-acceptable acid-addition salt thereof.

5. The compound which is 2-(5-propoxycarbonyl-N-methyl-3-aza-pentanamido)-5chlorobenzophenone or a pharmaceutically-acceptable acid-addition salt thereof.

* * * * *